United States Patent [19]

Kohama et al.

[11] Patent Number: 4,985,413

[45] Date of Patent: Jan. 15, 1991

[54] POISON BAIT FOR CONTROL OF NOXIOUS INSECTS

[75] Inventors: Takuji Kohama; Fumiyasu Minagawa; Goro Shinjo, all of Toyonaka; Kazuyuki Maeda, Nishinomiya, all of Japan

[73] Assignee: Sumitomo Chemical Company, Limited, Osaka, Japan

[21] Appl. No.: 164,108

[22] Filed: Mar. 4, 1988

[30] Foreign Application Priority Data

Mar. 6, 1987 [JP] Japan .................................. 62-52497

[51] Int. Cl.$^5$ ...................... A01N 57/00; A01N 57/18; A01N 47/10; A01N 37/34; A01N 25/00

[52] U.S. Cl. ........................................ 514/79; 514/113; 514/122; 514/125; 514/132; 514/141; 514/490; 514/521; 424/84

[58] Field of Search ................. 424/84; 514/79, 113, 514/122, 125, 132, 141, 490, 521

[56] References Cited

U.S. PATENT DOCUMENTS 4,049,460 9/1977 Broadbent .............................. 424/84
4,160,824 7/1976 Inazuka et al. ......................... 424/84

FOREIGN PATENT DOCUMENTS 3235931 3/1984 Fed. Rep. of Germany ........ 424/84
66193 8/1978 Japan .................................... 424/84
131223 4/1984 Japan .................................... 424/84
1733308 5/1986 Japan .................................... 424/84

OTHER PUBLICATIONS

The Merck Index cite #1925 (1983).
Hideakira Tsuji et al., Jap. J. Sanit. Zool., 20 (4), pp. 240–247 (1969).
Yuichiro Tabaru et al., Jap. J. Sanit. Zool., 25 (2), pp. 147–152 (1974).
11th Revision Commentary for Japanese Pharmacopeia, C-1475 (1986).

*Primary Examiner*—Douglas W. Robinson
*Assistant Examiner*—Raymond J. Henley, III
*Attorney, Agent, or Firm*—Birch, Stewart, Kolasch & Birch

[57] ABSTRACT

A composition which comprises (a) at least one insecticide selected from the group consisting of organic phosphorous insecticides, carbamate insecticides and pyrethroid insecticide, (b) crystalline cellulose and (c) crop product powders evaporated with (d) an essential oil and (e) a saccharide respectively in amounts of 0.1 to 10.0% by weight and 10.0 to 40.0% by weight based on the total weight of the composition, which is useful as a bait for the control of noxious insects.

19 Claims, No Drawings

POISON BAIT FOR CONTROL OF NOXIOUS INSECTS

This invention pertains to a poison bait for control of noxious insects, particularly cockroaches.

There have heretofore been commercially available some powdery poison baits for exterminating noxious insects such as cockroaches. These conventional powdery poison baits are however, practically disadvantageous and dangerous because they cause many problems from the standpoints of sanitation and daily use. For instance, they adhere to the hands on handling, continue to contaminate the surroundings even after being situated in desired places, or are erroneously taken as a food by infants and house animals.

In order to solve the above problems, a poison bait in a tablet form was put into the market, which comprises boric acid as the active ingredient. For assurance of the exterminating effect, however, these poison bait tablets contain boric acid in such a large amount as about 20 to 30% by weight. Because of this, they are still not safe for infants and house animals. In fact, it is reported that even a nursery powder containing boric acid in an amount of only 5% by weight accidentally produced the death of an infant (11th Japan Pharmacopoeia, C-1475 (1986)). In addition, the exterminating effect of boric acid against cockroaches is exerted quite belatedly, and it takes usually one week or more after feeding until their death, during which they are attacked by diarrhea and produce soft excrements so that their habitats and surroundings are considerably stained thereby.

There are also known some poison baits in tablets, which comprise as the active ingredient an insecticide chosen from organic phosphorus insecticides, carbamate insecticides, pyrethroid insecticides, etc. Since these insecticides have a much higher insecticidal potency than boric acid, their content in poison baits may be much smaller, so that the resulting poison baits are considerably safer. However, the insecticides each have a characteristic odor, and a tablet preparation comprising the same is apt to be refused by cockroaches. Thus, the feed attractant effect is significantly deteriorated, and naturally the exterminating effect is lowered. Further, the organic phosphorous insecticides or the carbamate insecticides can be readily hydrolyzed even with the slightest amount of water to produce a certain specific odor so that the feed attractant effect is likewise deteriorated and the exterminating effect is decreased. The hydrolysis results in the lowering of the content of the active ingredient itself, and the insecticidal effect is thus remarkably deteriorated.

As a result of an extensive study to overcome the drawbacks as seen in conventional poison baits for noxious insects including cockroaches, it has now been found that the incorporation of an essential oil and a saccharide into a poison bait composition comprising an insecticide chosen from organic phosphorus insecticides, carbamate insecticides and pyrethroid insecticides enhances markedly the stability of such insecticide and assures a better feed attractant effect and a higher insecticidal effect with a sufficient safety.

The present invention provides a bait composition for the control of noxious insects, particularly cockroaches, which comprises (a) at least one insecticide selected from the group consisting of organic phosphorus insecticides, carbamate insecticides and pyrethroid insecticide, (b) crystalline cellulose and (c) crop product powders incorporated with (d) an essential oil and (e) a saccharide respectively in amounts of 0.1 to 10.0% by weight and 10.0 to 40.0% by weight based on the total weight of the composition.

The insecticide as the component (a) may be chosen from organic phosphorus insecticides, carbamate insecticides and pyrethroid insecticides. As the organic phosphorus insecticides, there are exemplified caltinphos, chlorpyriphos, chlorpyriphosmethyl, cyanofenphos, cyanophos, diazinon, dichlorvos, fenitrothion, fenthion, malathion, naled, pirimiphosmethyl, prothiophos, pyridaphenthion, salithion, tetrachlorvinphos, trichlorfcn, bromophos, propetamphos, etc. Examples of the cartamate insecticides are BPMC, carbaryl, CPMC, ethiofencarb, MPMC, MTMC, promecarb, swep, propoxur, etc. Examples of the pyrethroid insecticides are cypermethrin, cyphenothrin, deltamethrin, fenpropathrin, fenvalerate, kadethrin, permethrin, phenothrin, proparthrin, resmethrin, ethofenprox, cyfluthrin, alphamethrin, tralomethrin, fulcythrinate, etc. Their geometrical or optical isomers may be also useo. The content of the insecticide may vary within a wide range depending upon the individual insecticide as used, the species of the insect to be treated, etc. Usually, it may be within a range of about 0.05 to 5.0% by weight to the total weight of the bait composition.

As the crystalline cellulose (b), there may be employed any one on the market, and a typical example is "Avicel ®" (Asahi Chemical Industry Co., Ltd.). This can be normally used in an amount of about 20.0 to 60.0% by weight to the total weight of the bait composition.

As the crop product powders (c), there are exemplified potato starch, sweet potato starch, corn starch, wheat flour, rice powder, corn powder, etc. These can be used in an amount of about 11.3 to 79.0% by weight on the basis of the total weight of the bait composition.

Examples of the essential oil as the component (d) are soybean oil, rapeseed oil, sesame oil, wheat germ oil, etc. The content of the essential oil in the bait composition is usually from about 0.1 to 10.0% by weight.

Examples of the saccharide as the component (e) are sucrose, glucose, D-fructose, lactose, black sugar, brown sugar, soft brown sugar, etc., among which black sugar, brown sugar and soft brown sugar are favorable. The content of the saccharide may be normally from about 10.0 to 40.0% by weight.

In formulation of the bait composition according to the invention, there may be, if necessary, incorporated an auxiliary agent(s) and/or an additive(s), more specifically an anti-oxidizing agent, a preservative, a mis-feed inhibitor, a flavoring agent, a feed attractant, etc.

As the anti-oxidizing agent, there may be exemplified erythorbic acid, sodium erythorbate, dibutyl hydroxytoluene, dl-alpha-tocophelol, nordihydroguaiaretic acid, methylhydroxyanisol, propyl gallate, guaiac resin, L-cysteine hydrochloride, etc. Examples of the preservative are benzoic acid, sodium benzoate, salicylic acid, diphenyl, sorbic acid, potassium sorbate, dehydroacetate, sodium dehydroacetate, isobutyl p-oxybenzoate, ispropyl p-oxybenzoate, ethyl p-oybenzoate, butyl p-oxybenzoate, propyl p-oxybenzoate, calcium propionate, sodium propionate, etc. As the mis-feed inhibitor, there may be used red pepper powders, Amaranth, Amaranth aluminium lake, Erythrosine, Erythrosine aluminium lake, New Coccine, Phloxine, Rose Bengal, Acid Red, Tartrazine, Tartrazine aluminium lake, Sunset Yellow FCF, Sunset Yellow FCF aluminium lake, Fast Green FCF, Fast Green FCF aluminium lake, Brilliant Blue FCF, Brilliant Blue FCF aluminium lake, Indigo Carmine, Indigo Carmine aluminium lake, beta-carotene, copper chlorophyll, etc. Further, such flavors as cheese, butter, peanut, peach, strawberry and milk are usable as the flavoring agent and also as the feed attractant.

According to the invention, the above mentioned active ingredients, optionally with the auxiliary agents and/or the additives, are formulated into a bait composition, preferably in any shaped form such as tablets. Although there is no particular limitation in formulation, the insecticidal components and an essential oil may be first combined at room temperature or under an elevated temperature, and other components such as crystalline cellulose, crop product powders and a saccharide may be incorporated therein, followed by mixing uniformly. The resultant mixture can be formulated into tablets of a desired size by a per se conventional manner.

The thus formulated bait composition exerts a remarkable insecticidal effect against a wide range of harmful insects, of which examples are cockroaches (Blattidae) such as *Periplaneta americana*, *Blattella germanica* and *Periplaneta fuliginosa*, ants (Formicidae) such as *Monomorium pharaonis*, *Monomorium nipponense*, *Lasius fuliginosus* and *Formica japonica* pillbug (Armadillidae), deathwatch and drugstore beetles (Anobiidae) such as *Lasioderma serricorne* and *Stegobium paniceum*, darkling beetles (Tenebrionidae) such as *Tribolium castaneum* and *Tribolium confusum* and cucujid beetles (Cucujidae) such as *Oryzaephilus surinamensis* and *Cryprolestes pusillus*, etc.

Practical embodiments for preparation of the insecticidal composition according to the invention are illustratively presented in the following Examples wherein % is percent by weight unless otherwise indicated.

EXAMPLES 1 to 6

Fenitrothion (0.5%) and sesame oil (3.0%) were mixed together, and a saccharide (as shown in Table 1) and potato starch (as shown in Table 1), crystalline cellulose (30.0%), butyl hydroxyanisol (0.03%) and dehydroacetic acid (0.1%) were added thereto, followed by mixing uniformly. The resultant mixture was tableted under a compression of 15 kg/cm$^2$ to make tablets, each weighing about 4 g (diameter, about 30 mm).

TABLE 1

| | (% by weight) Example | | | | | |
|---|---|---|---|---|---|---|
| Component | 1 | 2 | 3 | 4 | 5 | 6 |
| Saccharide | | | | | | |
| Black sugar | — | — | 10.00 | 20.00 | 30.00 | 40.00 |
| Brown sugar | — | 10.00 | — | — | — | — |
| Soft brown sugar | 10.00 | — | — | — | — | — |
| Potato starch | 56.37 | 56.37 | 56.37 | 46.37 | 36.37 | 26.37 |

The thus obtained tablets as a bait were subjected to an evaluation of stability of the active ingredients, feed attractant effect and insecticidal effect, of which the determinations were carried out in the following manner:

(1) Stability of the active ingredients:

The tablet was kept at 50° C. for 10 days and subjected to measurement of the residence rate of the active ingredient by gas chromatography. The tablet having a residence rate of not less than 80% is regarded satisfactory (O), while that having a residence rate of less than 80% is regarded unsatisfactory (X). The results are shown in Table 2.

(2) Feed attractant effect:

Fifty imagos of *Blattella germanica* (even numbers in male and female) were admitted in a container having a bottom area of 0.12 m$^2$ where the tablet as a bait as well as a solid bait as control were placed. An attractive rate of the test insect was calculated on the basis of the numbers of the insect attracted for a designated term. The attractant rate of not less than 70% is regarded satisfactory (+), while that of less than 70% is regarded unsatisfactory (—). The results are shown in Table 2.

(3) Insecticidal effect:

Evaluation of the insecticidal effect was conducted in the same manner as in the evaluation of the feed attractant effect, and the lethal rate was observed after continuous feeding for 24 hours. The lethal rate of not less than 80% is regarded satisfactory (+), while that less than 80% is regarded unsatisfactory (—). The results are shown in Table 2.

TABLE 2

| | (% by weight) Example | | | | |
|---|---|---|---|---|---|
| Evaluation | 1 | 2 | 3 | 4 | 5 |
| Stability of active ingredient | O | O | O | O | O |
| Feed attractant effect | | | | | |
| Immediately after tableting | + | + | + | + | + |
| After being kept at 50° C. for 10 days | + | + | + | + | + |
| Insecticidal effect | | | | | |
| Immediately after tableting | + | + | + | + | + |
| After being kept at 50° C. for 10 days | + | + | + | + | + |

COMPARATIVE EXAMPLE 1 TO 4

In the same manner as in Example 1 but changing the amounts of the saccharide and potato starch as shown in Table 3, there were prepared tablets as a bait. Stability, feed attractant effect and insecticidal effect were observed in the same manner as in Example 1, of which the results are shown in Table 3.

TABLE 3

| | (% by weight) Comparative Example | | | |
|---|---|---|---|---|
| Component and evaluation | 1 | 2 | 3 | 4 |
| Saccharide | | | | |
| Black sugar | — | — | — | 5.00 |
| Brown sugar | — | — | 5.00 | — |
| Soft brown sugar | — | 5.00 | — | — |
| Potato starch | 66.37 | 61.37 | 61.37 | 61.37 |
| Stability of active ingredient | O | O | O | O |
| Feed attractant effect | | | | |
| Immediately after tableting | — | — | + | + |
| After being kept at 50° C. for 10 days | — | — | — | — |
| Insecticidal effect | | | | |
| Immediately after tableting | — | + | + | + |
| After being kept at 50° C. for 10 days | — | — | — | — |

From the above results in Tables 1 through 3, it is understood that the amount of the saccharide is not so influential to the stability of the active ingredient, whereas its decrease does lead to the lowering of the feed attractant effect and insecticidal effect (cf. Comparative Example 1—no saccharide; Comparative Examples 2 to 4 —less than the defined range).

EXAMPLES 7 to 9

In the same manner as in Example 1, there were prepared, as a bait, tablets comprising an insecticide (as shown in Table 4), crysalline cellulose (30.0%), potato starch (as shown in Table 4), an essential oil (as shown in Table 4), soft brown sugar (10.0%), butyl hydroxyanisol (0.03%) and dehydroacetic acid (0.10%). Stability, feed attractant effect and insecticidal effect were observed in the same manner as in Example 1, of which the results are shown in Table 4.

COMPARATIVE EXAMPLES 5 to 7

In the same manner as in Examples 7 to 9 but changing the amounts of the essential oil and potato starch as shown in Table 4, there were prepared tablets as a bait, of which stability, feed attractant effect and insecticidal effect are also shown in Table 4.

TABLE 4

| | (% by weight) | | | | | |
|---|---|---|---|---|---|---|
| | Example | | | Comparative | | |
| Component | 7 | 8 | 9 | 5 | 6 | 7 |
| Insecticide | | | | | | |
| Cyanophos | 0.50 | — | — | 0.50 | — | — |
| Resmethrin | — | 0.30 | — | — | 0.30 | — |
| BPMC | — | — | 0.70 | — | — | 0.70 |
| Essential oil | | | | | | |
| Sesame oil | 2.00 | — | — | — | — | — |
| Wheat germ oil | — | 3.00 | — | — | — | — |
| Soybean oil | — | — | 4.00 | — | — | — |
| Potato starch | 57.37 | 56.57 | 55.17 | 59.37 | 59.57 | 59.17 |
| Stability of active ingredients | O | O | O | X | X | X |
| Feed attractant effect | | | | | | |
| Immediately after tableting | + | + | + | — | + | — |
| After being kept at 50° C. for 10 days | + | + | + | — | — | — |
| Insecticidal effect | | | | | | |
| Immediately after tableting | + | + | + | + | + | — |
| After being kept at 50° C. for 10 days | + | + | + | — | — | — |

It is understood from the above results, the tablets of Examples 7 to 9 are superior to those of Comparative Example 5 to 7 not comprising an essential oil in stability of the active ingredient, feed attractant effect and insecticidal effect.

EXAMPLES 10 TO 15

In the same manner as in Example 1, there were prepared, as a bait, tablets comprising the components as shown in Table 5. Stability, feed attractant effect and insecticidal effect were observed in the same manner as in Example 1, of which the results are shown in Table 5.

TABLE 5

| | (% by weight) | | | | | |
|---|---|---|---|---|---|---|
| | Example | | | | | |
| | 10 | 11 | 12 | 13 | 14 | 15 |
| Component | | | | | | |
| Insecticide | | | | | | |
| Diazinon | 1.00 | — | — | — | — | — |
| Chlorpyriphos | — | 0.30 | — | — | — | — |
| Permethrin | — | — | 0.05 | — | — | — |
| Phenothrin | — | — | — | 5.00 | — | — |
| MPMC | — | — | — | — | 0.60 | — |
| CPMC | — | — | — | — | — | 0.80 |
| Crystalline cellulose | 25.00 | 60.00 | 20.00 | 25.00 | 45.00 | 35.00 |
| Saccharide | | | | | | |
| Black sugar | 25.00 | — | — | — | 40.00 | — |
| Brown sugar | — | 10.00 | — | 30.00 | — | — |
| Soft brown sugar | — | — | 20.00 | — | — | 30.00 |
| Essential oil | | | | | | |
| Wheat germ oil | 10.00 | — | — | 0.10 | — | — |
| Corn oil | — | 5.00 | — | — | 3.00 | — |
| Sesame oil | — | — | 0.50 | — | — | 2.00 |
| Starch | | | | | | |
| Corn starch | 39.50 | — | — | 39.39 | — | 31.58 |
| Potato starch | — | 24.55 | 59.45 | — | 11.30 | — |
| Additive | | | | | | |
| Dibutylhydroxytoluene | — | 0.55 | — | 0.01 | — | — |
| Nordihydroguaiaretic acid | — | — | — | — | — | 0.02 |
| Dehydroacetic acid | — | 0.10 | — | — | 0.10 | 0.10 |
| Red pepper powder | 0.50 | — | — | 0.50 | — | 0.50 |
| Red No. 1 | Slight | — | — | Slight | Slight | — |
| Evaluation | | | | | | |
| Stability of active ingredient | O | O | O | O | O | O |
| Feed attractant effect | | | | | | |
| Immediately after tableting | + | + | + | + | + | + |
| After being kept at 50° C. for 10 days | + | + | + | + | + | + |
| Insecticidal effect | | | | | | |
| Immediately after tableting | + | + | + | + | + | + |
| After being kept at 50° C. for 10 days | + | + | + | + | + | + |

It is understood from the above results that the tablets according to the invention are quite satisfactory in stability of the active ingredient, feed attractant effect and insecticidal effect.

What is claimed is:

1. A bait composition for the control of noxious insects which comprises (a) at least one insecticide selected from the group consisting of organic phosphorous insecticides, carbamate insecticides and pyrethroid insecticides, (b) crystalline cellulose, (c) crop product powders, (d) an essential oil, and (e) a saccharide, wherein the components (a), (b), (c), (d) and (e) are contained respectively in amounts of 0.05 to 5.0% by weight, 20.0 to 60.0% by weight, 11.3 to 79.0% by weight, 0.1 to 10.0% by weight, and 10.0 to 40.0% by weight based on the total weight of the composition and the composition is in a tablet form.

2. The composition according to claim 1, wherein the crop product powders are selected from the group consisting of potato starch, sweet potato starch, corn starch, wheat flours, rice powders and corn powders.

3. The composition according to claim 1, wherein the saccharide is selected from the group consisting of sucrose, glucose, D-fructose, lactose, black sugar, brown sugar and soft brown sugar.

4. The composition according to claim 1, wherein the organic phosphorous insecticide is a member selected from the group consisting of calbinphos, chlorpyriphos, chlorpyriphosmethyl, cyanofenphos, cyanophos, diazinon, dichlorvos, fentitrothion, fenthion, malathion, naled, pirimiphosmethyl, prothiophos, pyridaphenthion, salithion, tetrachlorvinphos, trichlorfon, bromophos and protetamphos.

5. The composition according to claim 1, wherein the carbamate insecticide is a member selected from the group consisting of BPMC, carbaryl, CPMC, ethiofencarb, MPMC, MTMC, promecarb, and propoxur.

6. The composition according to claim 1, wherein the pyrethroid insecticide is a member selected from the group consisting of cypermethrin, cyphenothrin, deltamethrin, fenpropathrin, fenvalerate, kadethrin, permethrin, phenothrin, proparthrin, resmethrin, ethofenprox, cyfluthrin, alpha-methrin, tralomethrin and fulcythrinate.

7. The composition according to claim 1, wherein the essential oil is a member selected from the group consisting of soybean oil, rapeseed oil, sesame oil, and wheat germ oil.

8. The composition according to claim 1, wherein noxious insects are selected from the group consisting of cockroaches (Blattidae), ants (Formicidae), pillbug (Armadillidae), deathwatch and drugstore beetles (Anobiidae), darkling beetles (Tenebrionidae) and cucujid beetles (Cucujidae).

9. The composition according to claim 1, further comprising an antioxidizing agent.

10. The composition according to claim 9, wherein the antioxidizing agent is a member selected from the group consisting of erythorbic acid, sodium erythorbate, dibutyl hydroxytoluene, dlalphatocophelol, alphatocophelol, nordihydroguaiaretic acid, methylhydroxyanisole, propyl gallat, guaiac resin and L-cysteine hydrochloride.

11. The composition according to claim 1, further comprising a preservative.

12. The composition according to claim 11, wherein the preservative is a member selected from the group consisting of benzoic acid, sodium benzoate, salicyclic acid, diphenyl, sorbic acid, potassium sorbate, dehydracid, sodium dehydroacetate, isobutyl p-oxybenzoate, isopropyl p-oxybenzoate, ethyl p-oxybenzoate, butyl p-oxybenzoate, propyl p-oxybenzoate, calcium propionate and sodium propionate.

13. The composition according to claim 1, further comprising a misfeed inhibitor.

14. The composition according to claim 13, wherein the misfeed inhibitor is a member selected from the group consisting of red pepper powders, Amaranth, Amaranth aluminum lake, Erythrosine, Erythrosine aluminum lake, New Coccine, Phloxine, Rose Bengal, Acid Red, Tartrazine, Tartrazine aluminum lake, Sunset Yellow FCF, Sunset Yellow FCF aluminum lake, Fast Green FCF, Fast Green FCF aluminum lake, Brilliant Blue FCF, Brilliant Bule FCF aluminum lake, Indiggo Carmine, Indigo Carmine aluminum lake, beta-carotene, copper and chlorophyll.

15. The composition according to claim 1, further comprising a flavoring agent.

16. The composition according to claim 15, wherein the flavoring agent is a member selected from the group consisting of cheese flavor, butter flavor, peanut flavor, peach flavor, strawberry flavor and milk flavor.

17. The composition according to claim 1, further comprising a feed attractant.

18. A method for controlling noxious insects which comprises applying an insecticidally effective amount of the composition according to claim 1 to an area containing said insects.

19. The method according to claim 18, wherein the insects are selected from the group consisting of cockroaches (Blattidae), ants (Formicidae), pillbug (Armadillidae), deathwatch and drugstore beetles (Anobiidae), darking beetles (Tenebrionidae) and cucujid beetles (Cucujidae).

* * * * *